US008414639B2

(12) United States Patent
Tischler

(10) Patent No.: US 8,414,639 B2
(45) Date of Patent: Apr. 9, 2013

(54) CLOSED-CELL FLEXIBLE STENT HYBRID

(75) Inventor: Brian Tischler, New Brighton, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1011 days.

(21) Appl. No.: 12/169,515

(22) Filed: Jul. 8, 2008

(65) Prior Publication Data

US 2010/0010619 A1    Jan. 14, 2010

(51) Int. Cl.
*A61F 2/06* (2006.01)
(52) U.S. Cl. ............... 623/1.16; 623/1.12; 623/1.18; 623/1.2
(58) Field of Classification Search .......... 623/1.11, 623/1.12, 1.16, 1.18, 1.2
See application file for complete search history.

(56) References Cited

U.S. PATENT DOCUMENTS

| | | | |
|---|---|---|---|
| 4,580,568 A * | 4/1986 | Gianturco | 606/198 |
| 5,441,515 A | 8/1995 | Khosravi et al. | |
| 5,443,500 A * | 8/1995 | Sigwart | 623/1.17 |
| 5,824,053 A * | 10/1998 | Khosravi et al. | 623/1.15 |
| 6,048,360 A | 4/2000 | Krosravi et al. | |
| 6,312,463 B1 * | 11/2001 | Rourke et al. | 623/1.39 |
| 6,348,065 B1 | 2/2002 | Brown et al. | |
| 6,623,518 B2 * | 9/2003 | Thompson et al. | 623/1.11 |
| 6,878,153 B2 | 4/2005 | Linder et al. | |
| 6,896,696 B2 | 5/2005 | Doran et al. | |
| 7,041,129 B2 | 5/2006 | Rourke et al. | |
| 7,122,059 B2 | 10/2006 | Rourke et al. | |
| 2004/0254630 A1 | 12/2004 | Yang | |
| 2007/0156226 A1 | 7/2007 | Chew et al. | |

* cited by examiner

*Primary Examiner* — Kathleen Holwerda
*Assistant Examiner* — Sarah W Aleman
(74) *Attorney, Agent, or Firm* — Vidas, Arrett & Steinkraus, P.A.

(57) ABSTRACT

A stent has a first stent body and a second stent body. The first stent body is a rolled stent having a first end and a second end and the second stent body is a tubular stent. The stent has a deployed state, the stent being within a body lumen in the deployed state. The second stent body at least partially disposed within the first stent body when the stent is in the deployed state so that the first end of the first stent body overlaps the second end of the first stent body for a first overlap length.

12 Claims, 14 Drawing Sheets

CLOSED-CELL FLEXIBLE STENT HYBRID

CROSS-REFERENCE TO RELATED APPLICATIONS

Not Applicable

STATEMENT REGARDING FEDERALLY SPONSORED RESEARCH

Not Applicable

BACKGROUND OF THE INVENTION

A stent is a medical device introduced to a body lumen and is well known in the art. Typically, a stent is implanted in a blood vessel at the site of a stenosis or aneurysm endoluminally, i.e. by so-called "minimally invasive techniques" in which the stent in a radially reduced configuration, optionally restrained in a radially compressed configuration by a sheath and/or catheter, is delivered by a stent delivery system or "introducer" to the site where it is required. The introducer may enter the body from an access location outside the body, such as through the patient's skin, or by a "cut down" technique in which the entry blood vessel is exposed by minor surgical means.

Stents, grafts, stent-grafts, vena cava filters, expandable frameworks, and similar implantable medical devices are radially expandable endoprostheses which are typically intravascular implants capable of being implanted transluminally and enlarged radially after being introduced percutaneously. Stents may be implanted in a variety of body lumens or vessels such as within the vascular system, urinary tracts, bile ducts, fallopian tubes, coronary vessels, secondary vessels, etc. They may be self-expanding, expanded by an internal radial force, such as when mounted on a balloon, or a combination of self-expanding and balloon expandable (hybrid expandable).

Stents may be created by methods including cutting or etching a design firm a tubular stock, from a flat sheet which is cut or etched and which is subsequently rolled or from one or more interwoven wires or braids.

The art referred to and/or described above is not intended to constitute an admission that any patent, publication or other information referred to herein is "prior, art" with respect to this invention. In addition, this section should not be construed to mean that a search has been made or that no other pertinent information as defined in 37 C.F.R. §156(a) exists.

All US patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

BRIEF SUMMARY OF THE INVENTION

In at least one embodiment, the invention is directed to a stent comprising a first stent body and a second stent body. In some embodiments, the first stent body is a rolled sheet and the second stent body is a tubular stent. The first stent body is disposed about at least a portion of the second stent body. In other embodiments, the stent is used for carotid artery stenting.

In at least one embodiment, the invention is directed to a catheter configured to deploy an embodiment of a stent comprising a first stent body and a second stent body. In some embodiments, the first stent body of the stent is disposed about a distal region of the catheter and the second stent body of the stent is disposed about the first stent body and a tether extends through a plurality of openings of the stent along the longitudinal length of the stent to the proximal end of the catheter.

In at least one embodiment, the invention is directed to a catheter configured to deploy another embodiment of a stent comprising a first stent body and a second stent body. In some embodiments, the first stent body of the stent is disposed about a first region of the catheter and the second stent body of the stent is disposed about a second region of the catheter, where the first and second regions are separated by a portion of the catheter.

In at least one embodiment, the invention is directed to a method of deploying a stent comprising a first stent body and a second stent body. In some embodiments, the first and second stents bodies are deployed simultaneously using a first catheter embodiment. In some embodiments, the first and second stent bodies are deployed sequentially using another catheter embodiment.

These and other embodiments which characterize the invention are pointed out with particularity in the claims annexed hereto and forming a part hereof. However, for further understanding of the invention, its advantages and objectives obtained by its use, reference can be made to the drawings which form a further part hereof and the accompanying descriptive matter, in which there is illustrated and described an embodiments of the invention.

BRIEF DESCRIPTION OF THE SEVERAL VIEWS OF THE DRAWING(S)

A detailed description of the invention is hereafter described with specific reference being made to the drawings FIG. 1 is a cross-sectional view of a stent comprising a first stent body and a second stent body in a tubular, uncrimped state.

DETAILED DESCRIPTION OF THE INVENTION

Figure 1:
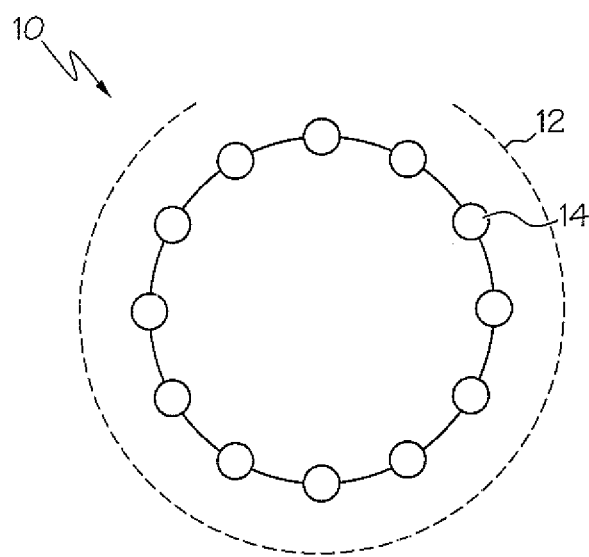

While this invention may be embodied in many different forms, there are described in detail herein specific embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

In at least one embodiment, the stent 10 has a tubular shape and comprises a first stent body 12 and a second stent body 14, where the first stent body 12 is disposed about at least a portion of the second stent body 14 when the stent 10 is deployed in a body lumen. In some embodiments, the first and second stent bodies 12, 14 are engaged to one another at one or more locations. In at least one embodiment, the stent 10 is used for carotid artery stenting. In some embodiments, the stent 10 is constructed and arranged so that the stent 10 prevents the plaque from a carotid lesion from breaking free and causing a stroke. In one embodiment, the scaffolding of the stent 10 is small, i.e. the size of the cells is small, to prevent plaque from a carotid lesion from breaking free and causing a stroke.

In at least one embodiment, the first stent body 12 is a rolled sheet stent and the second stent body 14 is a tubular stent. In some embodiments, the first stent body 12 has a closed cell configuration and the second stent body 14 has an open cell configuration. In other embodiments, the first stent body 12 provides vessel coverage and the second stent 14 body provides radial strength. In other embodiments, the struts 16 comprising the first stent body 12 have an axial diameter that is less than the axial diameter of the struts 16 comprising the second stent body 14. The axial diameter is the thickness of the struts 16. In at least one embodiment, the first stent body 12 is self-expandable and the second stent body 14 is self-expandable. In some embodiments, the first stent body 12 is self-expandable and the second stent body 14 is balloon expandable. In other embodiments, the first stent body 12 is balloon expandable and the second stent body 14 is balloon expandable.

Figure 2:
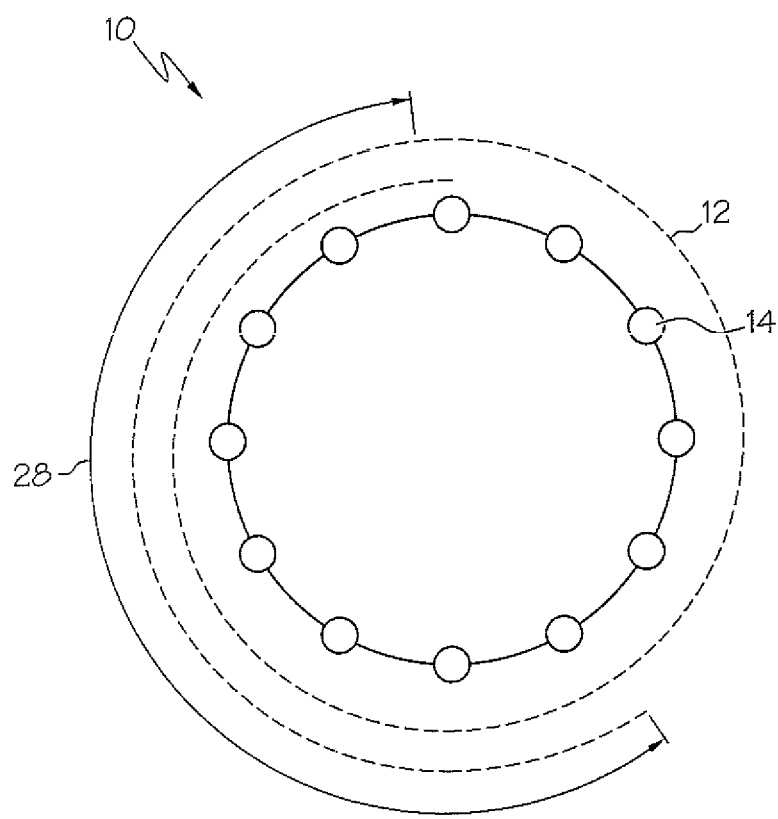
FIG. 2 is a cross-sectional view of the stent of FIG. 1 in a crimped state.
Figure 3:
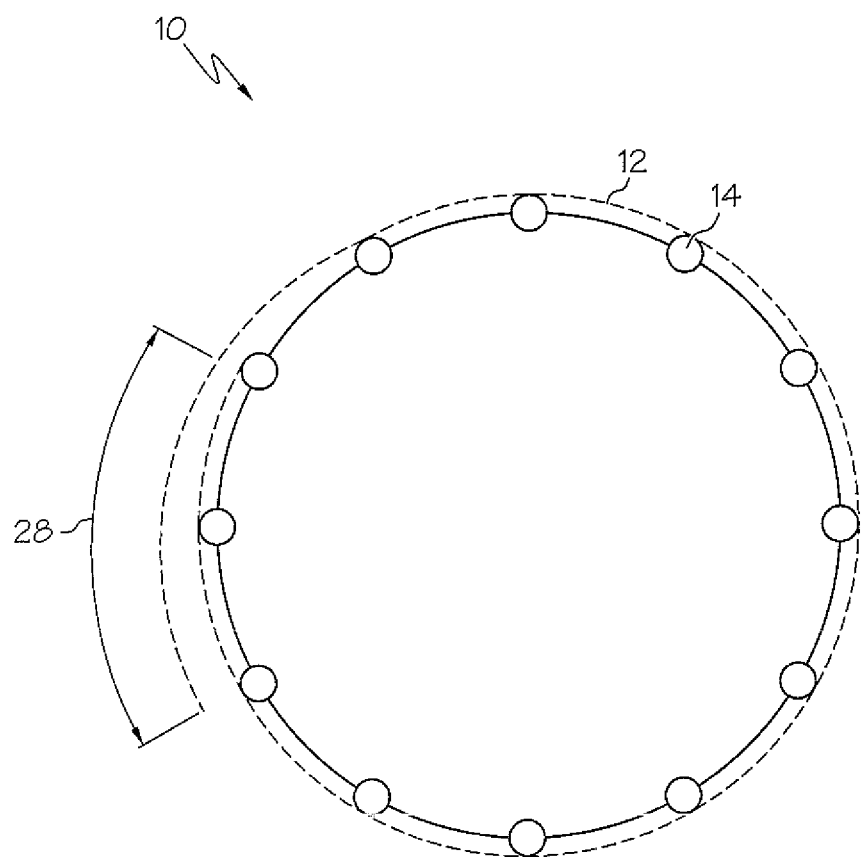
FIG. 3 is a cross-sectional view of the stent of FIG. 1 in a deployed state.
Figure 4:
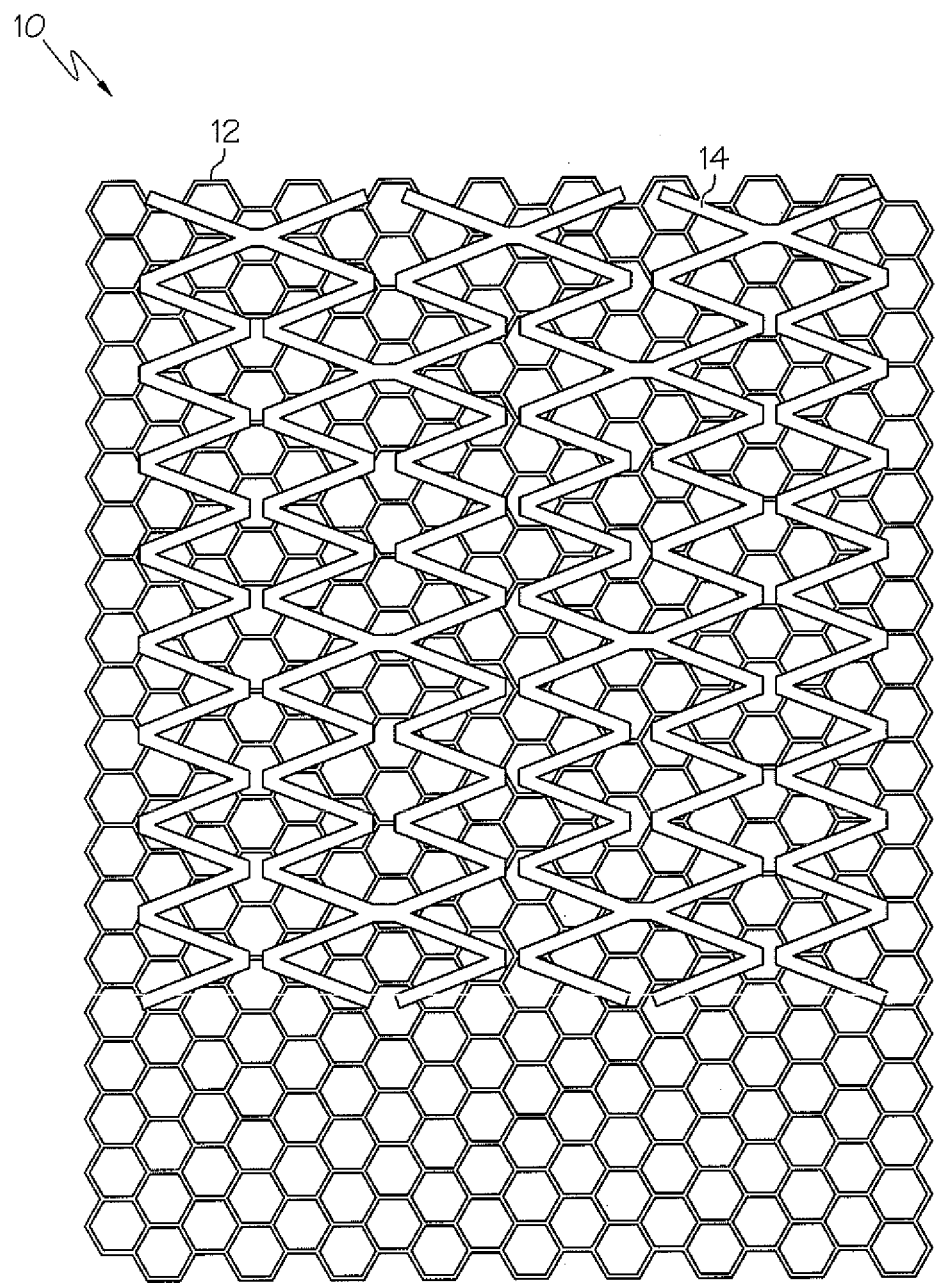
FIG. 4 is a flat view of the stent of FIG. 1.

FIGS. 1-3 are cross-sectional views of the stent 10 in different states. In FIG. 1, the stent 10 is in an unconstrained of uncrimped state. Note that in the unconstrained/uncrimped state, the ends 26 of the first stent body 12 do not overlap. The stent 10 of FIG 1, which has been cut along the longitudinal axis of the stent 10 and flattened, is shown in flat view in FIG. 4. In FIG. 2, the stent 10 is in a constrained or crimped state. Note that when the stent 10 is in a constrained/crimped state, the ends of the first stent body 12 overlap 28. It is within the scope of the invention for the overlap 28 to have any length. In some embodiments, the length of the overlap 28 is at least equal to half the circumference of the first stent body 12. In FIG. 3, the stent 10 is in a deployed state. In some embodiments, the length of the overlap 28 when the stent 10 is in the deployed state is less than the length of the overlap 28 when the stent 10 is in a constrained state. This can be seen when FIGS. 2 and 3 are compared.

Figure 5:
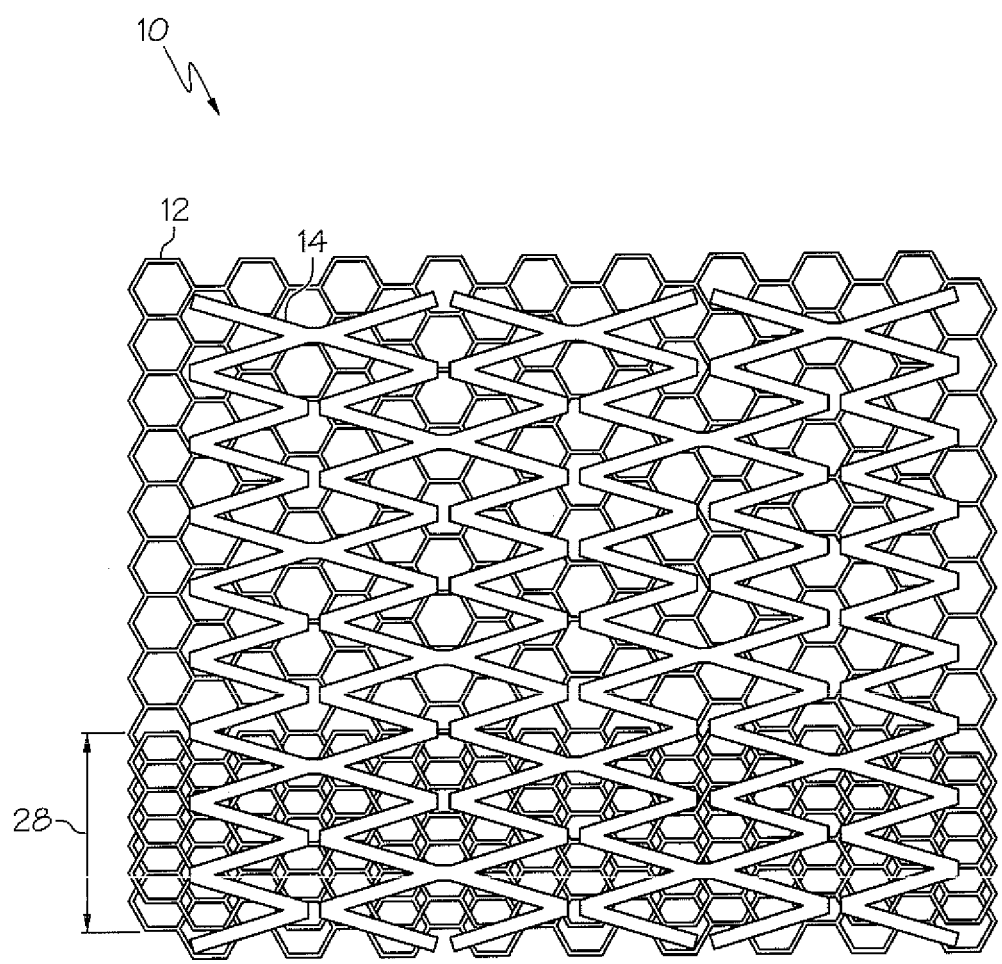
FIG. 5 is a flat view of a stent in the crimped state.
Figure 6:
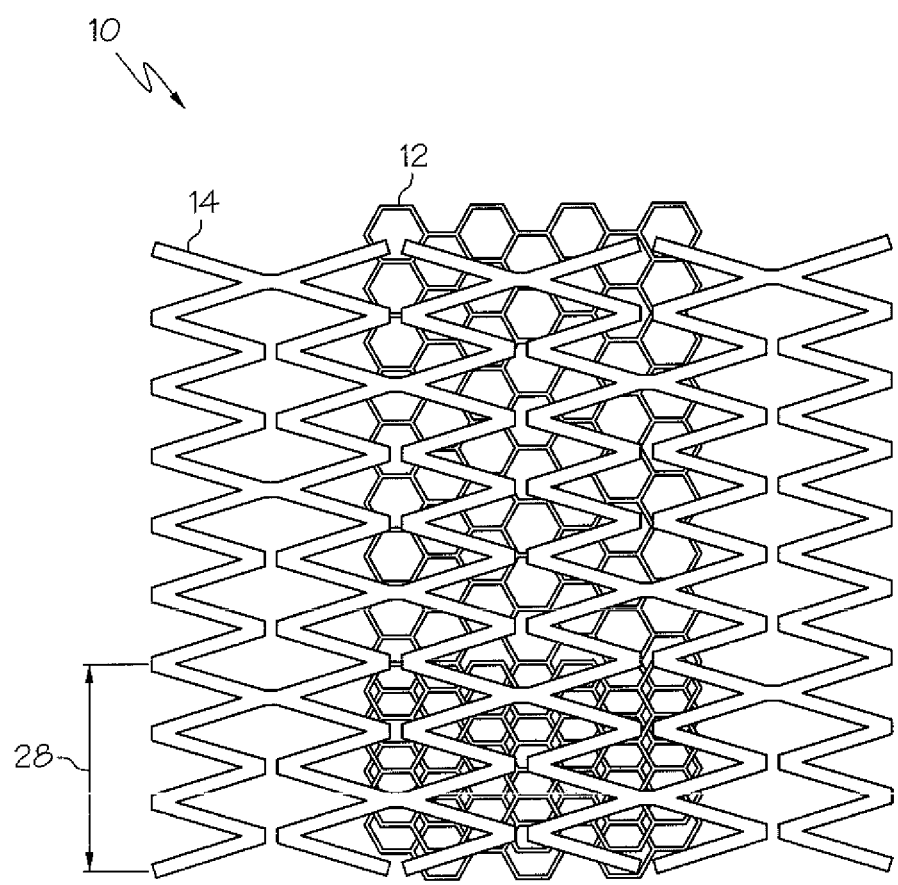
FIG. 6 is a flat view of another stent in a crimped state, with the second stent body positioned on top of the first stent body.
Figure 7:
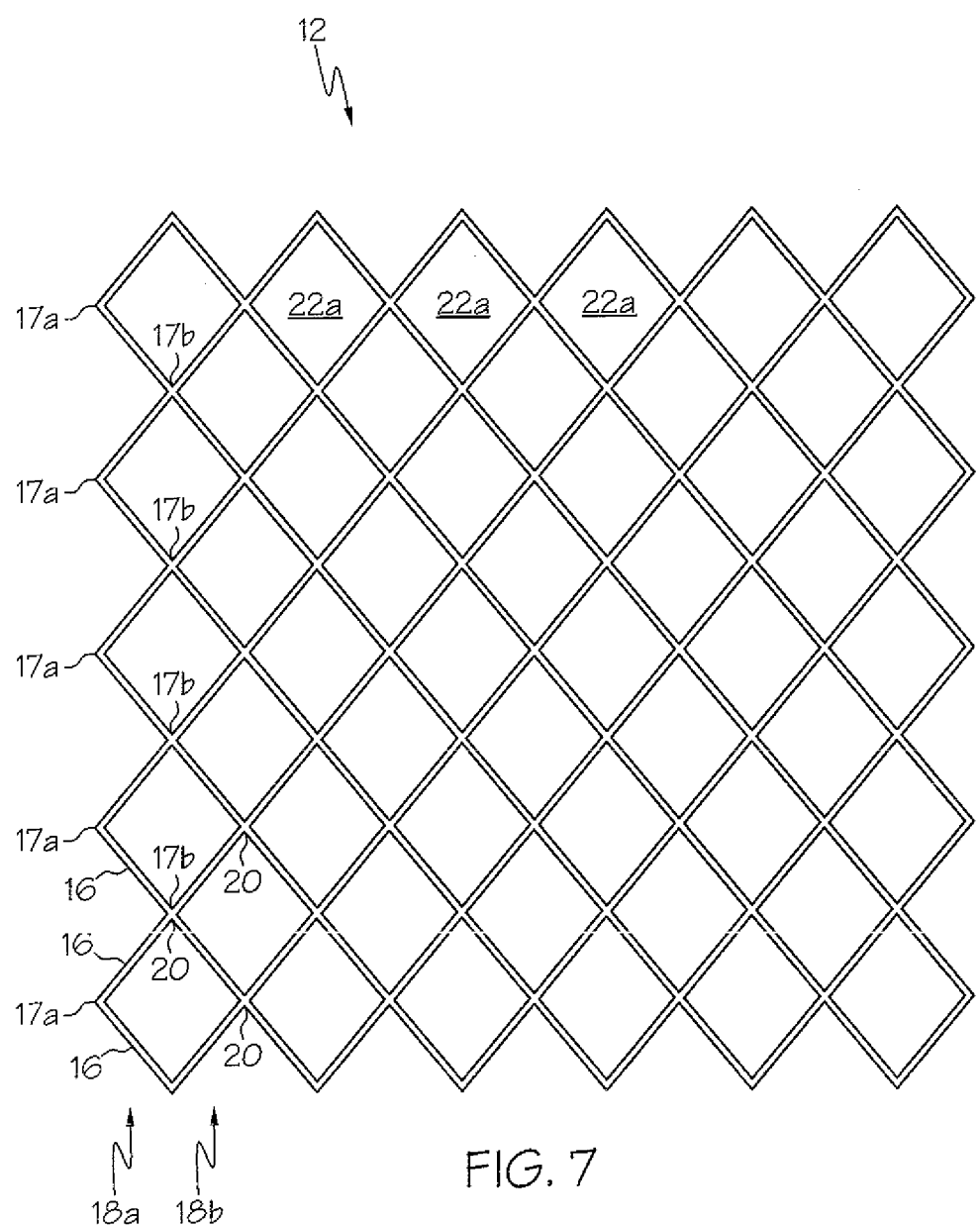
FIG. 7 is a flat view of a configuration of the first stent body of the stent.
Figure 8:
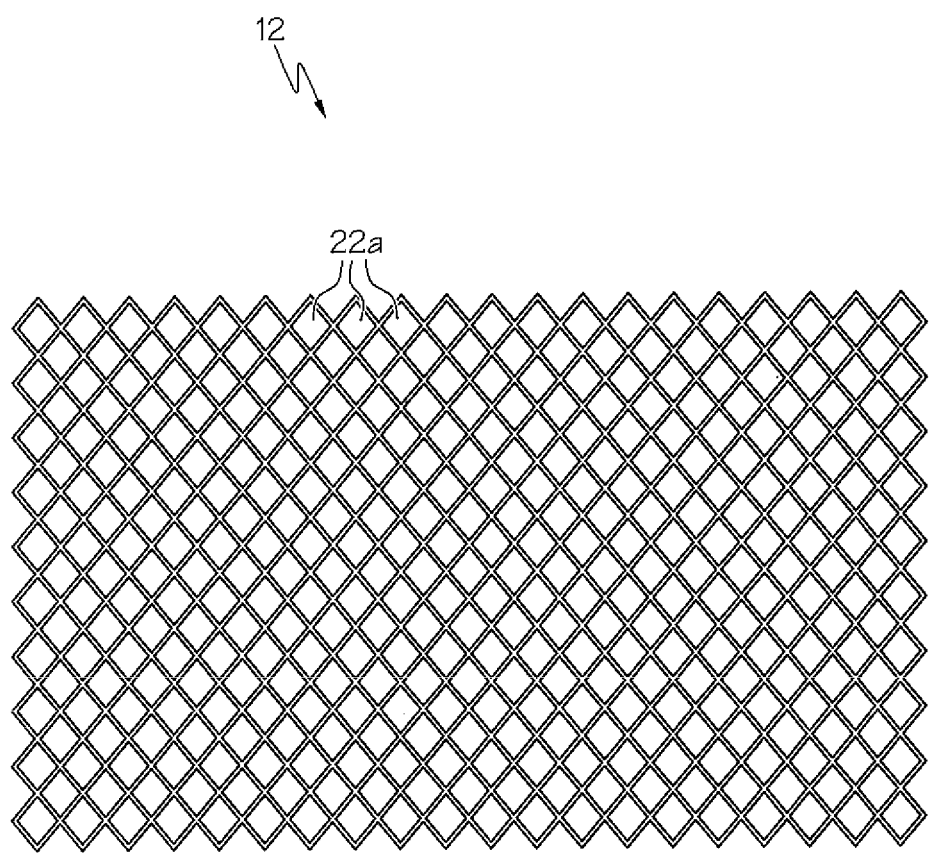
FIG. 8 is a flat view of the configuration shown in FIG. 7 having a different density.
Figure 9:
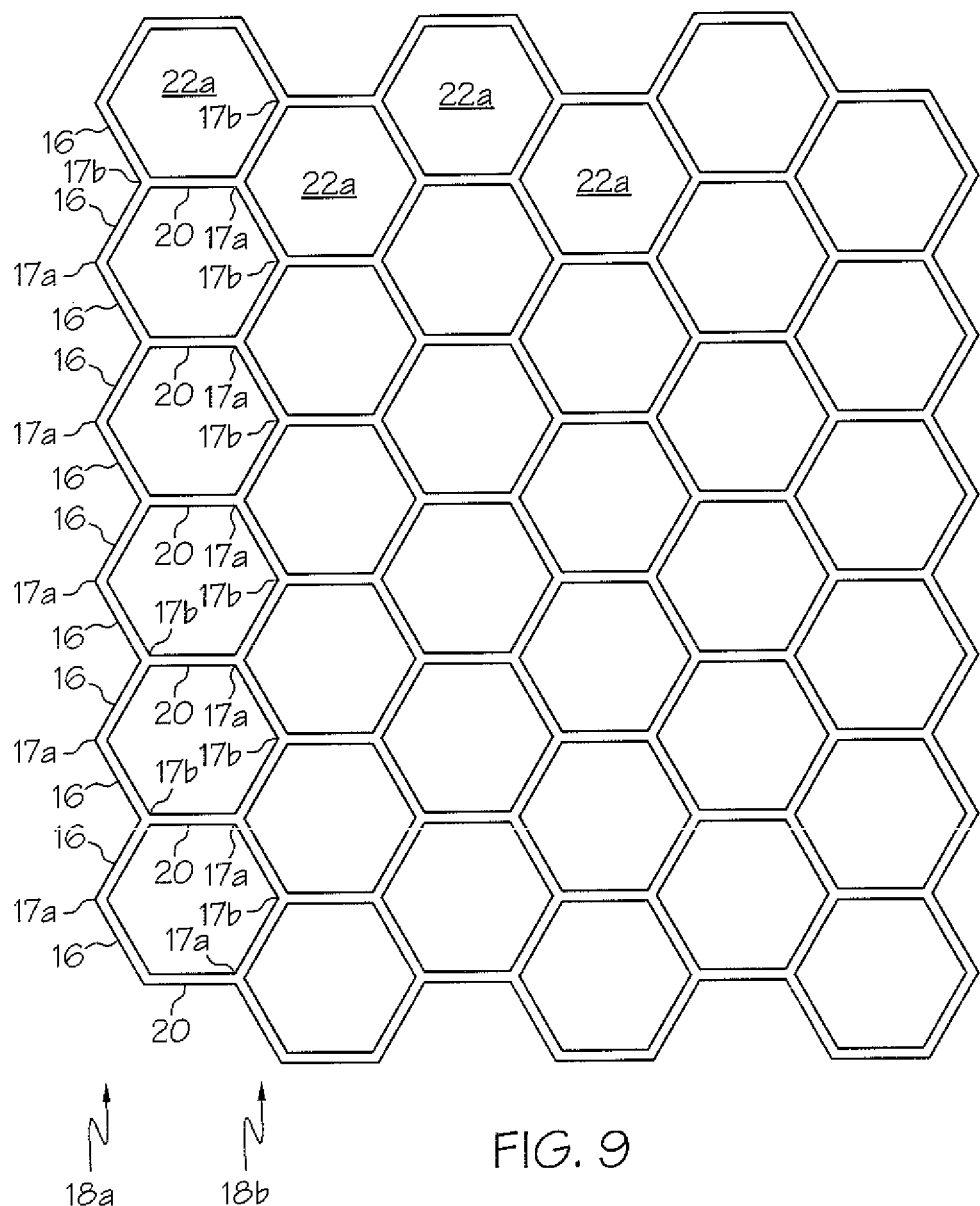
FIG. 9 is a flat view of a configuration for the first stent body of the stent.
Figure 10:
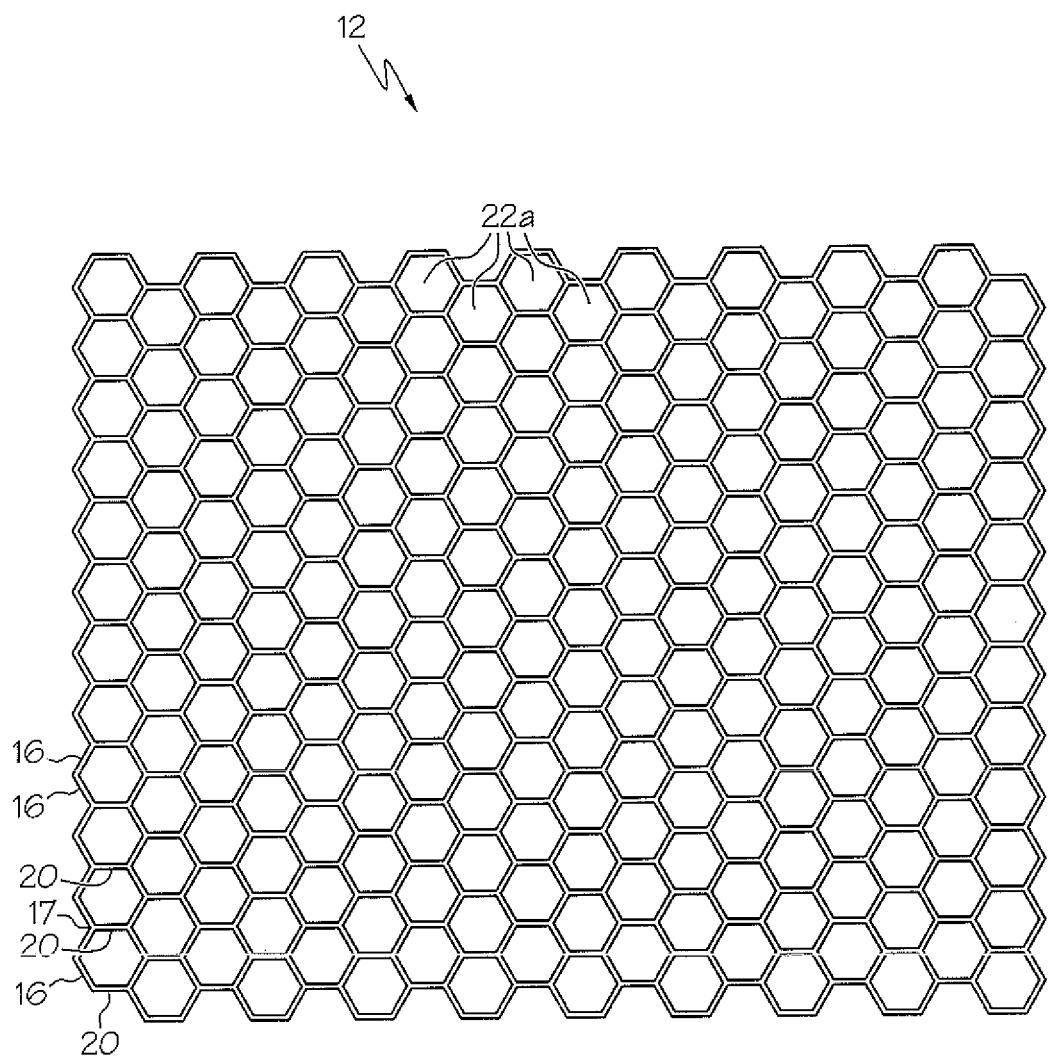
FIG. 10 is a flat view of the configuration shown in FIG. 9 having a different density.

FIG. 5 is a flat view of a constrained/crimped stent 10 which has been cut along the longitudinal axis of the sent 10 and flattened. Note that a flat view of the stent 10 of FIG. 3 would be similar to that shown in FIG. 5 except for the length of the overlap 28. The flat view of the stent 10 in FIG. 6 is similar to the flat view in FIG. 5 except that the longitudinal length of the first stent body 12 is less than the longitudinal length of the second stent body 14. Thus, in some embodiments, the longitudinal length of the first stent body 12 is greater than the longitudinal length of second stent body 14, as shown, for example, in FIG. 4. In other embodiments, the longitudinal length of the first stent body 12 is less than the longitudinal length of the second stent body 14, as shown, for example, in FIG. 6. In still other embodiments, the longitudinal length of the first stent body 12 is the same as the longitudinal length of the second stent body 14.

It is within the scope of the invention for the first stent body 12 of the stent 10 to have any configuration FIGS. 7-12 show some non-limiting examples of configurations for the first stent body 12. In some embodiments, the first stent body 12 comprises a closed cell design, as shown, for example, in FIG. 7. A closed cell design is characterized by a connector 20 extending between every other turn 17 of adjacent circumferential bands 18. Turns 17 include peaks 17a and troughs 17b. As used in this application and shown in the figures, a peak 17a is a turn 17 extending in a proximal direction and a trough 17b is a turn 17 extending in a distal direction. It is within the scope of the invention for the connector 20 to be a peak to peak connector 20 where connector 20 engages a peak 17a on a circumferential band 18a and a peak 17a on an adjacent circumferential band 18b, a peak to trough connector 20, shown for example in FIG. 9, where the connector 20 engages a peak 17a on a circumferential band 18a and a trough 17b on an adjacent circumferential band 18b, or a trough to trough connector 20 where the connector 20 engages a trough 17b on a circumferential band 18a and a trough 17b on an adjacent circumferential band 18b.

Figure 11:
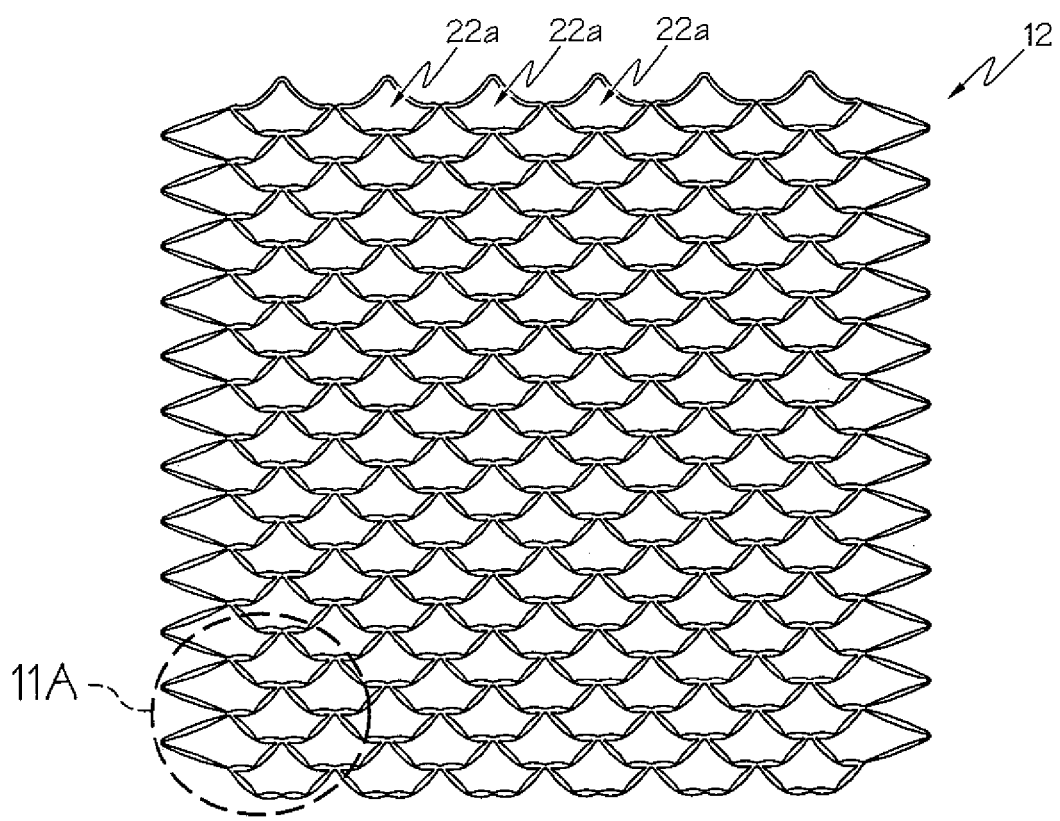
FIG. 11 is a flat view of a configuration for the first stent body of the stent.
Figure 11A:
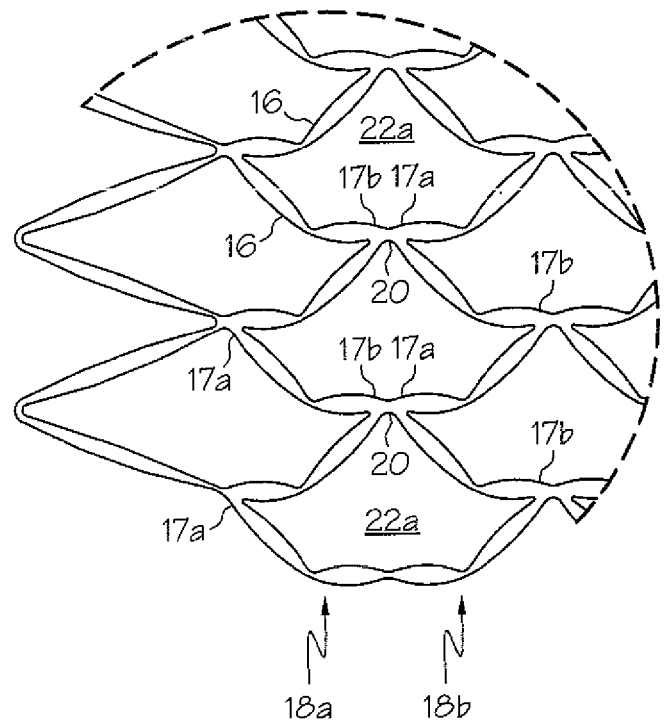
Figure 12:
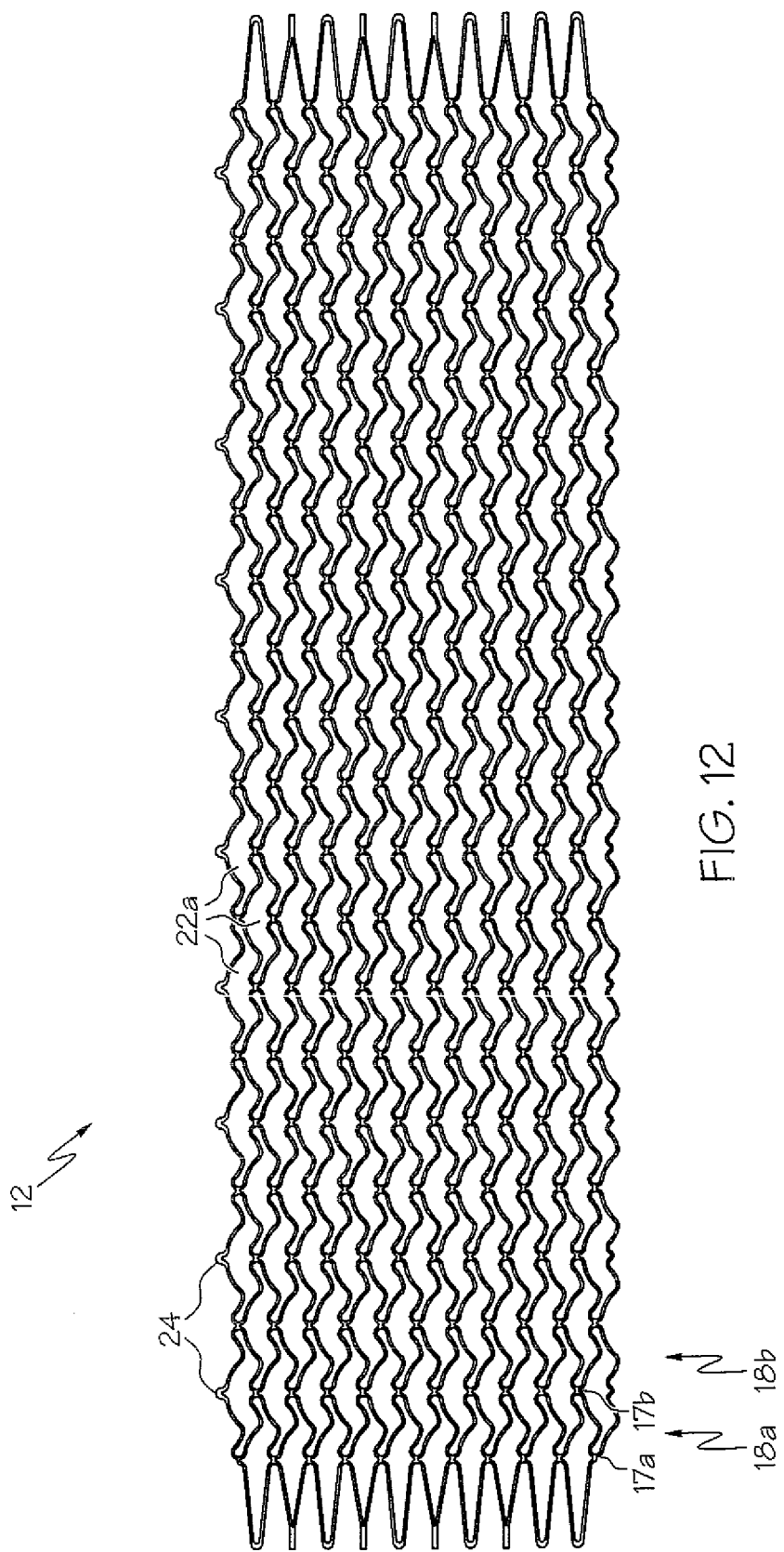
FIG. 12 is a flat view of a configuration for the first stent body of the stent.

It is within the scope of the invention for the first stent body 12 to have any density of cells 22, i e. the number of cells 22 per area. For example, in FIG. 7, the density of cells 22 is less than the density of cells 22 in FIG. 8. In some embodiments, the density of the cells 22 is configured so that when the stent 10 is deployed in a body lumen that has plaque, the first stent body 12 prevents plaque from entering the body lumen. In at least one embodiment, the first stent body 12 has teeth 24, as shown in FIG. 12. Rolled stents having teeth 24 are discussed in greater detail in U.S. Pat. No. 6,048,360 to Khosiavi et al., entitled Methods of Making and Using Coiled Sheet Graft for Single and Bifurcated Lumens, hereby incorporated by reference in its entirety. The stent pattern shown in FIG. 11 is discussed in greater detail in U.S. Pat. No. 7,122,059 to Rourke et. al., entitled Selectively Thinned Coiled-sheet Stents and Methods for Making Them, hereby incorporated by reference in its entirety. The stent pattern shown in FIG. 12 is discussed in greater detail in U.S. Patent Application No. 2004/0254630 to Yang, entitled Coiled Sheet Stent with Flexible Mesh Design, hereby incorporated by reference in its entirety.

It is within the scope of the invention for the first stent body 12 of the stent 10 to be made from shape memory materials, plastically deformable marerials, expanded polytetrafluoroethylene (ePTFE), biocompatible materials, grafts, or coverings, biodegradable materials and any combination thereof.

Examples of shape memory marerials include, but are not limited to, superelastic Nitinol or spring steel. In the case of shape memory materials, the first stent body 12 may be provided with a memorized shape and then deformed to a reduced diameter shape. The first stent body 12 may restore itself to its memorized shape upon being heated to a transition temperature and having any restraints removed therefrom.

Examples of suitable biocompatible materials include, but are not limited to, one or more polymers, one or more metals or combinations of polymer(s) and metal(s). Examples of suitable marerials include biodegradable materials that are also biocompatible. By biodegradable is meant that a material will undergo breakdown or decomposition into harmless compounds as part of a normal biological process. Suitable biodegradable materials include polylactic acid, polyglycolic acid (PGA), collagen or other connective proteins or natural materials, polycaprolactone, hylauric acid, adhesive proteins, co-polymers of these materials as well as composites and combinations thereof and combinations of other biodegradable polymers. Other polymers that may be used include polyester and polycarbonate copolymers. Examples of suitable metals include, but are not limited to, stainless steel, titanium, tantalum, platinum, tungsten, gold and alloys of any of the above-mentioned metals. Examples of suitable alloys include platinum-iridium alloys, cobalt-chromium alloys including Elgiloy and Phynox, MP35N alloy and nickel-titanium alloys, for example, Nitinol.

In at least one embodiment, the first stent body 12 may be created by methods including cutting or etching a design from a tubular stock, from a flat sheet which is cut or etched and which is subsequently rolled or from one or mote interwoven wires or braids. Any other suitable technique which is known in the art or which is subsequently developed may also be used to manufacture the first stent body 12 of the stent 10.

Figure 13:
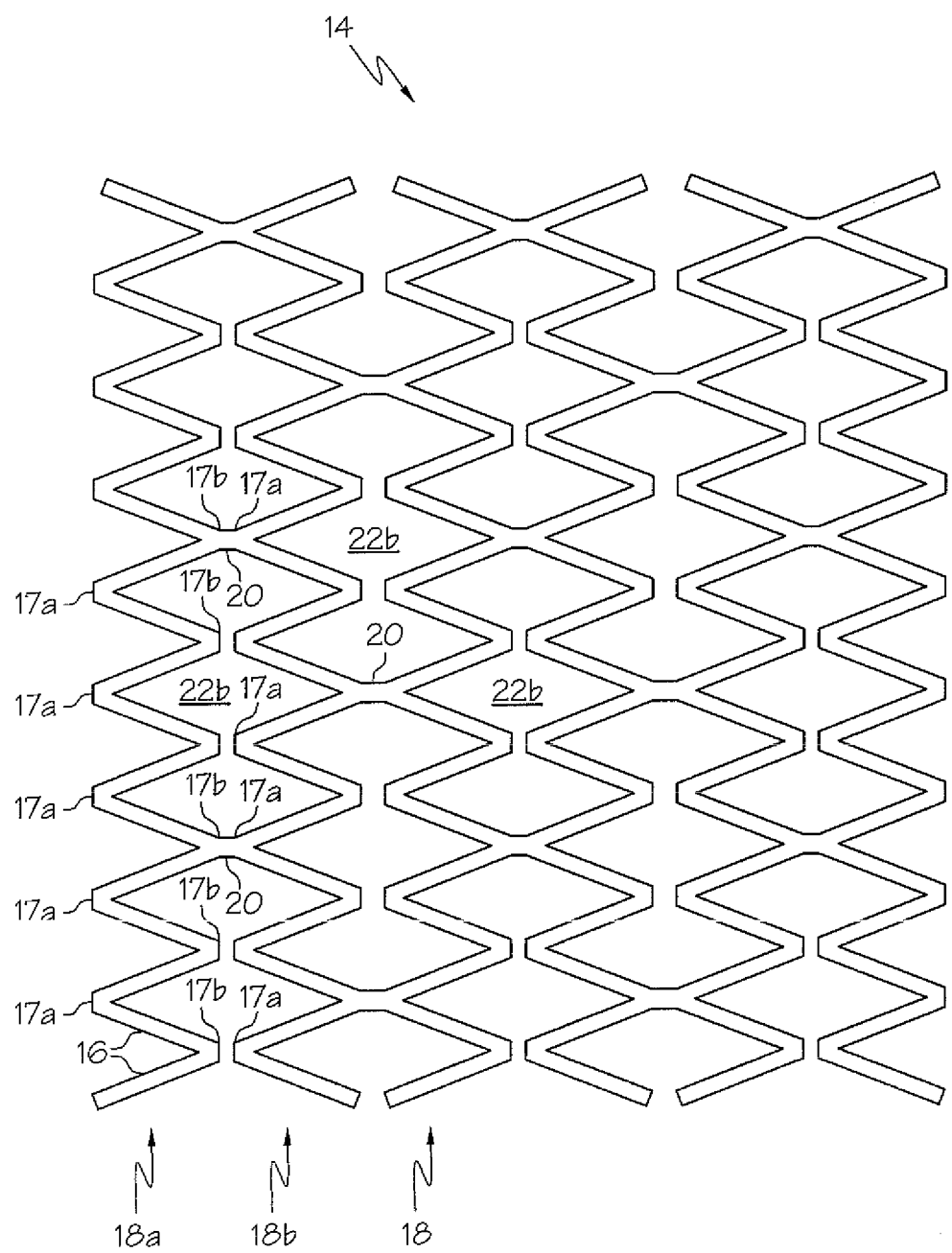
FIG. 13 is a flat view of a configuration for the second stent body of the stent.

It is within the scope of the invention for the second stent body 14 of the stent 10 to have any configuration. FIG. 13 is a non-limiting example of a second stent body 14 having a plurality of struts 16 forming a plurality of circumferential bands 18, where adjacent circumferential bands 18 are engaged by a plurality of connectors 20. Other examples of configurations for the second stent body 14 can be seen in U.S. Pat. No. 6,348,065 to Brown, entitled Longitudinally Flexible Stent and U.S. Pat. No. 6,896,696 to Doran et al, entitled Flexible and Expandable Stent, each of which are hereby incorporated by reference in their entirety. In some embodiments, the second stent body 14 comprises an open cell design. An open cell design is characterized by connectors 20, engaging adjacent circumferential bands 18a,b, being separated from circumferentially adjacent connectors 20 by at least two turns 17a,b, as shown, for example in FIG. 13. It is within the scope of the invention for the connectors 20 to be peak to peak connectors, peak to trough connectors, as shown, for example in FIG. 13, or trough to trough connectors.

In at least one embodiment, the second stent body 14 of the stent 10 is made of shape memory materials such as superelastic Nitinol or spring steel, or of materials which are plastically deformable. In the case of shape memory materials, the second stent body 14 may be provided with a memorized shape and then deformed to a reduced diameter shape. The second stent body 14 may restore itself to its memorized shape upon being heard to a transition temperature and having any restraints removed therefrom. In at least one embodiment, the second stent body 14 may be created by methods including cutting or etching a design from a tubular stock, from a flat sheet which is cut or etched and which is subsequently rolled to form a tubular stent or from one or more interwoven wires or braids. Any other suitable technique which is known in the art or which is subsequently developed may also be used to manufacture the second stent body 14 of the stent 10.

Figure 14:
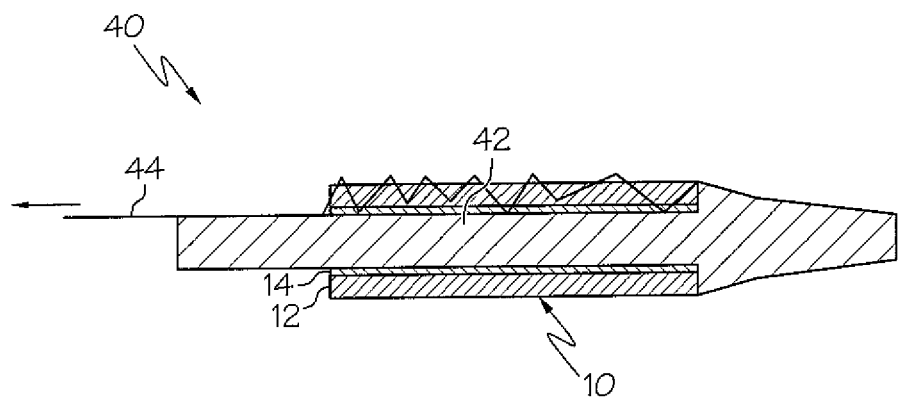
FIG. 14 is a side view of a catheter assembly that has a tether for the deployment of the stent of FIG 2.
Figure 17:
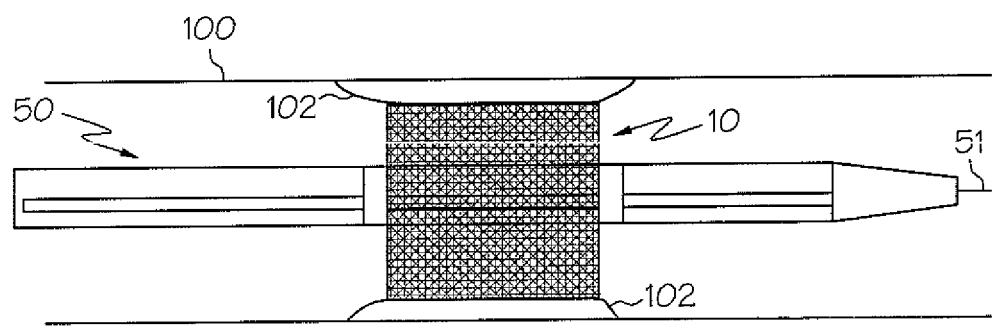
FIG. 17 is a side view of the catheter assembly of FIG. 16 after the second stent body of the stent has been deployed within the vessel.

The invention is also directed to a catheter assembly 40 used to deploy the stent 10 and a method of deploying the stent 10. The catheter assembly 40 is shown in FIG. 14. In this embodiment, the distal end region of the catheter assembly 40 comprises a stent receiving region 42. The second stent 14 of the stent 10 is disposed about the stent receiving region 42 and the first stent 12 of the stent 10 is disposed about the second stent 14. The catheter assembly 40 further comprises a tether 44 that extends from the distal end region to the proximal end region of the catheter assembly 50. As shown in FIG. 17, the tether 44 extends through the stent bodies 12 and/or 14 of the stent 10, thereby maintaining the stent 10 in position on the stent receiving region 42. In some embodiments, the tether 44 extends through the overlap region 28 of the stent 10. The tether 44 can be a wire, a string, and any combination thereof.

To deliver a stent 10 with catheter assembly 40, the catheter 40 is advanced to a desired location in a body lumen, e.g. a vessel. Once the stent 10 is positioned at the desired location, the tether 44 is pulled in a proximal direction so that the tether 44 disengages from the stent 10, disposed about the stent receiving region 42 of the catheter 40. In some embodiments, the stent 10 deploys when the tether 44 is disengaged from the stent 10. In other embodiments, the first stent body 12 of the stent 10 is deployed when the tether 44 is disengaged from the stent 10 and the second stent body 14 is deployed by a balloon as is known in the art. In one embodiment, the balloon forms the stent receiving region 42 of the catheter 40.

Materials that can be used to make the tether 44 include, but are not limited to, biocompatible materials, biodegradable materials, polymers, metals, alloys, and any combination thereof. Suitable biocompatible materials including one or more polymers, one or more metals or combinations of polymer(s) and metal(s). Examples of suitable materials include biodegradable materials that are also biocompatible. By biodegradable is meant that a material will undergo breakdown or decomposition into harmless compounds as part of a normal biological process. Suitable biodegradable materials include polylactic acid, polyglycolic acid (PGA), collagen or other connective proteins or natural materials, polycaprolactone, hylauric acid, adhesive proteins, co-polymers of these materials as well as composites and combinations thereof and combinations of other biodegradable polymers. Other polymers that may be used include polyester and polycarbonate copolymers. Examples of suitable metals include, but are not limited to, stainless steel, titanium, tantalum, platinum, tungsten, gold and alloys of any of the above-mentioned metals. Examples of suitable alloys include platinum-iridium alloys, cobalt-chromium alloys including Elgiloy and Phynox, MP35N alloy and nickel-titanium alloys, for example, Nitinol.

Figure 15:
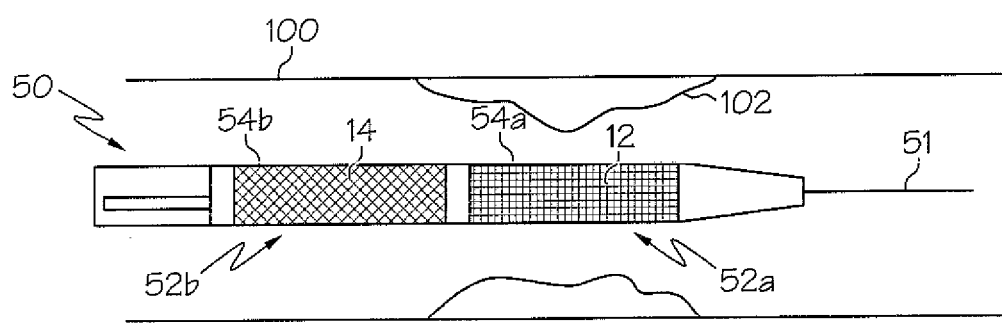
FIG. 15 is a side view of another catheter assembly for the sequential delivery of another embodiment of the stent of FIG. 2 within a vessel.

In at least one embodiment, the invention is also directed to another catheter assembly 50 to deliver an embodiment of the stent 10 where the first and second stent bodies 12,14 are delivered sequentially and a method of delivering the stent 10 using the catheter assembly 50 A shown in FIG. 15, the catheter assembly 50 has two stent receiving regions 52a,b which are longitudinally separated from one another by a portion of the catheter assembly 50 The first stent receiving region 52a is positioned distally to the second stent receiving region 52b. In some embodiments, the first stent body 12 is disposed about the first stent receiving region 52a and the second stent body 14 is disposed about the second stent receiving region 52b. In other embodiments, the first stent body 12 is disposed about the second stent receiving region 52b and the second stent body 14 is disposed about the first stent receiving region 52a.

In some embodiments, the catheter assembly 50 is used to deliver a stent 10 where the first and second stent bodies 12,14 are self-expandable. In one embodiment, a first sheath 54a keeps the first stent body 12 disposed about the first stent receiving region 52a and a second sheath 54b keeps the second stent body 14 disposed about the second stent receiving region 52b. The optional sheaths 54a,b are shown in FIG. 15. The sheaths 54a,b can be engaged to the catheter assembly 50 in any suitable manner.

In other embodiments, the catheter assembly 50 is used to deliver a stent 10 where the first stent body 12 is self-expandable and the second stent body 14 is balloon expandable. In this embodiment, one of the two stent receiving regions 52 is disposed about a balloon and one of the stent receiving regions 52 has a sheath 54 disposed thereabout.

Figure 16:
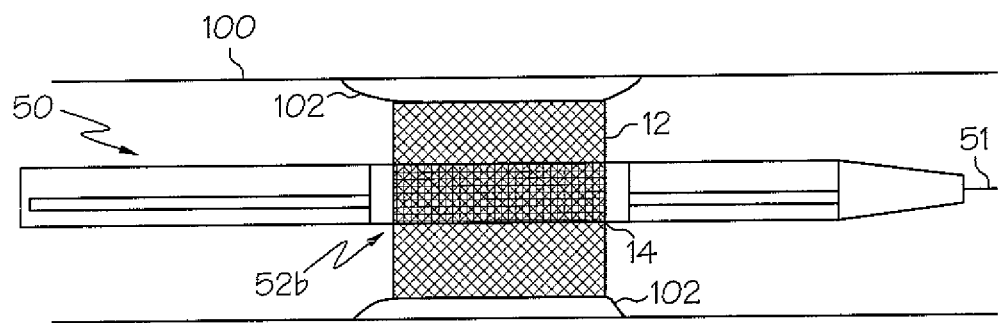
FIG. 16 is a side view of the catheter assembly of FIG. 15 after the first stent body of the stent has been deployed within the vessel.

In at least one embodiment, the first and second stent bodies 12,14 of the stent 10 are deployed sequentially, as shown for example in FIGS. 15-17. The catheter assembly 50 is advanced to a desired location within a body lumen, e.g. a vessel. The catheter assembly 50 is positioned so that the first stent body 12, which is disposed about the first stent receiving legion 52a, is at the desired location in the body lumen Once the first stent body 12 is at the desired location, the first sheath 54a is withdrawn away from the first stent body 12, which is self-expanding, so that the first stent body 12 is deployed into the body lumen. Then the catheter assembly 50 is positioned so that the second stent body 14, disposed about the second stent receiving region 52b, is located at least partially within the deployed first stent body 12. Once the second stent body 14 is at the desired location, the second stent body 14 is deployed. In some embodiments, sheath 54b is withdrawn away from the second stent body 14, which is self-expanding, so that the second stent body 14 is deployed into the body lumen. In other embodiments, the second stent body 14 is a balloon expandable stent and is deployed into the body lumen when the balloon is expanded. In this embodiment, the second stent receiving region 52b is disposed about a balloon.

Thus, after the first and second stent bodies 12,14 are deployed in the body lumen, the first stent body 12 is disposed about at least a portion of the second stent body 14. Note that the relative position of the first and second stent bodies 12,14 to one another depends on the position of the catheter assembly 50 when the second stent body 14 is deployed. Thus, for example, the stent 10 configuration of FIG. 6 is obtained if the catheter assembly 50 is positioned so that the center of second stent body 14 is aligned with the center of the first stent body 12. It is also within the scope of the invention for the center of the second stent body 14 to be offset, either distally or proximally, from the center of the first stent body 12.

In at least one embodiment, the stent 10 and/or the catheter assembly 40,50 has one or more areas, bands, coatings, members, etc. that is (are) detectable by imaging modalities such as X-Ray, MRI, ultrasound, etc. In some embodiments, at least a portion of the stent 10 and/or portions of the catheter assembly 40,50 adjacent to the stent 10 is at least partially radiopaque.

In at least one embodiment at least a portion of the stent 10 is configured to include one or more mechanisms for the delivery of a therapeutic agent In some embodiments, the first stent body 12 has at least one mechanism to deliver a therapeutic agent. In other embodiments, the second stent 14 body has at least one mechanism to deliver at least one therapeutic agent In some embodiment, both the first stent body 12 and the second stent body 14 have at least one mechanism to deliver a therapeutic agent. Often the therapeutic agent will be in the form of a coating or other layer (or layers) of material placed on a surface region of the stent, which is adapted to be released at the site of the stent's implantation or areas adjacent thereto.

A therapeutic agent may be a drug or other pharmaceutical product such as non-genetic agents, genetic agents, cellular material, etc. Some examples of suitable non-genetic therapeutic agents include but are not limited to: anti-thrombogenic agents such as heparin, heparin derivatives, vascular cell growth promoters, growth factor inhibitors, Paclitaxel, etc. Where an agent includes a genetic therapeutic agent, such a genetic agent may include but is not limited to: DNA, RNA and their respective derivatives and/or components; hedgehog proteins, etc. Where a therapeutic agent includes cellular material, the cellular material may include but is not limited to: cells of human origin and/or non-human origin as well as their respective components and/or derivatives thereof. Where the therapeutic agent includes a polymer agent, the polymer agent may be a polystyrene-polyisobutylene-polystyrene triblock copolymer (SIBS), polyethylene oxide, silicone rubber and/or any other suitable substrate.

The following numbered statements characterize at least one of the embodiments described above:

1. A method of deploying a stent comprising:
   advancing a catheter assembly in a body lumen, the catheter assembly comprising a first stent receiving and a second stent receiving region, the first and second stent receiving legions longitudinally separated from one another, a first stent body of the stent being disposed about the first stent receiving region, the first stent body being a rolled stent having a first end and a second end, a second stent body of the stent being disposed about the second stent receiving region, the second stent body being a tubular stent;
   deploying the first stent body at a desired location in the body lumen;
   positioning the catheter assembly so that the second stent body is at least partially disposed within the deployed first stent body; and
   deploying the second stent body, the second stent body being at least partially disposed within the first stent body after the stent is deployed.

2. The method of claim 1, the first stent body defining a plurality of closed cells and the second stent body defining a plurality of open cells.

3. The method of claim 1, the first stent body being self-expandable and the second stent body being self-expandable.

4. The method of claim 1, further comprising withdrawing the catheter assembly from the body lumen.

The above disclosure is intended to be illustrative and not exhaustive. This description will suggest many variations and alternatives to one of ordinary skill in this art. The various elements shown in the individual figures and described above may be combined or modified for combination as desired. All these alternatives and variations are intended to be included within the scope of the claims where the term "comprising" means "including, but not limited to".

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the invention. Those skilled in the art may recognize other equivalents to the specific embodiment described herein which equivalents are intended to be encompassed by the claims attached hereto.

The invention claimed is:

1. A stent, the stent comprising:
   a first stent body, the first stent body being a rolled stent having a first end and a second end, the first stent body comprising a plurality of circumferential bands and a plurality of connectors, each circumferential band comprising a plurality of struts engaged one to another by turns, wherein some of the turns in a circumferential band are peaks and others are troughs, adjacent circumferential bands being engaged by a plurality of connectors separated one from another by a single turn;
   a second stent body, the second stent body being a tubular stent, the second stent comprising a plurality of circumferential bands and a plurality of connectors, each circumferential band comprising a plurality of struts engaged one to another by turns, wherein some of the turns in a circumferential band are peaks and others are troughs, adjacent circumferential bands being engaged by a plurality of connectors separated one from another by at least two turns; and
   the stent having a deployed state, the second stent body at least partially disposed within the first stent body when the stent is in the deployed state, the first end of the first stent body overlapping the second end of the first stent body for a first overlap length when the stent is in the deployed state.

2. The stent of claim 1, the first stent body being self-expandable and the second stent body being self-expandable.

3. The stent of claim 1, the stent having a crimped state, the first end of the first stent body overlapping the second end of the first stent body when the stent is in the crimped state, the overlap having a second overlap length, second overlap length being greater than the first overlap length.

4. The stent of claim 1, the first stent body having a radial thickness, the second stent body having a radial thickness, the radial thickness of the first stent body being less than the radial thickness of the second stent body.

5. The stent of claim 1, at least a portion of the first stent body being engaged to a portion of the second stent body.

6. The stent of claim 1, the stent having an uncrimped state wherein the first and second ends of the first stent body do not overlap, the stent being in the uncrimped state before being in the deployed state.

7. A catheter assembly, the catheter assembly comprising:
   a catheter, the catheter having a stent receiving region; and
   a stent, the stent being disposed about the stent receiving region, the stent comprising a first stent body and a second stent body,
   the first stent body being a rolled stent, the first stent body comprising a plurality of circumferential bands, and a plurality of connectors, each circumferential band comprising a plurality of struts engaged one to another by turns, wherein some of the turns in a circumferential band are peaks and others are troughs, adjacent circumferential bands being engaged by a plurality of connectors separated one from another by a single turn,
   the second stent body being a tubular stent, the second stent comprising a plurality of circumferential bands and a plurality of connectors, each circumferential band comprising a plurality of struts engaged one to another by turns, wherein some turns in a circumferential band are peaks and others are troughs, adjacent circumferential bands being engaged by a plurality of connectors separated one from another by at least two turns,
   at least a portion of the second stent body being disposed within at least a portion of the first stent body.

8. The catheter assembly of claim 7, further comprising a tether, the tether having a distal end region, the distal end region of the tether being engaged to the stent.

9. The stent of claim 7, the first stent body comprising a first end, a second end, the stent having an uncrimped state wherein the first and second ends of the first stent body do not overlap, the stent having a crimped state wherein the first and second ends of the first stent body overlap a first distance, the stent being in the crimped state when disposed about the stent receiving region, the stent having a deployed state wherein the first and second ends of the first stent body overlap a second distance less than the first distance, the stent being in the deployed state after being in the crimped state.

10. A method of deploying a stent comprising:
    advancing a catheter assembly to a desired location in a body lumen, the catheter assembly comprising a stent receiving region and a tether, a first stent body of the stent being disposed about the stent receiving region, the first stent body being a tubular stent having a first end and a second end, the first stent body comprising a plurality of circumferential bands and a plurality of connectors, each circumferential band comprising a plurality of struts engaged one to another by turns, wherein some of the turns in a circumferential band are peaks and others are troughs, adjacent circumferential bands being engaged by a plurality of connectors separated one from another by at least two turns, a second stent body of the stent being disposed about at least a portion of the first stent body, the second stent body being a rolled stent, the second stent body comprising a plurality of circumferential bands and a plurality of connectors, each circumferential band comprising a plurality of struts engaged one to another by turns, wherein some of the turns in a circumferential band are peaks and others are troughs, adjacent circumferential bands being engaged by a plurality of connectors separated one from another by a single turn, the second stent body being self-expandable, the tether being interlaced in between the cells of the stent, the tether extending from the stent receiving region to a proximal end of the catheter assembly;
    pulling the tether in a proximal direction so that the tether is no longer interlaced in between the cells of the stent; and
    deploying the stent into the body lumen.

11. The method of claim 10, the first stent body being self-expandable and the second stent body being self-expandable, so that when the tether is pulled in a proximal direction the stent deploys.

12. The method of claim 10, further comprising withdrawing the catheter assembly from the body lumen.

\* \* \* \* \*